United States Patent [19]

Sasabe et al.

[11] Patent Number: 5,393,403
[45] Date of Patent: Feb. 28, 1995

[54] PROBE USING A MIXED SUB-ELECTRODE FOR MEASURING THE ACTIVITY OF CARBON IN MOLTON IRON

[75] Inventors: Minoru Sasabe, No. 22-20-501, 8-chome, Konakadai, Chiba-shi, Chiba-ken; Yoshihiko Kawai, Tokyo; Yoshiteru Kikuchi, Tokyo; Toshio Takaoka, Tokyo; Hiromi Seno, Osaka; Chikayashi Furuta, Osaka; Toshio Nagatsuka, Osaka, all of Japan

[73] Assignees: NKK Corporation, Tokyo; Minoru Sasabe, Chiba; Osaka Sanso Kogyo Ltd., Osaka, all of Japan

[21] Appl. No.: 67,417

[22] Filed: May 25, 1993

Related U.S. Application Data

[63] Continuation of Ser. No. 765,544, Sep. 25, 1991, abandoned.

[30] Foreign Application Priority Data

Sep. 26, 1990 [JP] Japan .................................. 2-254133

[51] Int. Cl.$^6$ .......................................... G01N 27/416
[52] U.S. Cl. ...................................... 204/422; 204/421
[58] Field of Search ........................ 204/421, 422, 423

[56] References Cited

U.S. PATENT DOCUMENTS

| | | | |
|---|---|---|---|
| 3,652,427 | 3/1972 | Flood et al. | 204/153.18 |
| 3,855,082 | 12/1974 | Hufer | 204/153.1 |
| 4,065,371 | 12/1977 | Rodgers et al. | 204/433 |
| 4,428,770 | 1/1984 | Worrell et al. | 75/45 |
| 4,830,727 | 5/1989 | Sasabe et al. | 204/412 |
| 5,192,404 | 3/1993 | Fray et al. | 204/153.19 |

*Primary Examiner*—John Niebling
*Assistant Examiner*—William T. Leader
*Attorney, Agent, or Firm*—Nields & Lemack

[57] ABSTRACT

A probe having the inventive composition, it is possible to measure the activity of the solute carbon which could not be measured by the prior art because there did not exist solid oxide or solid composite oxide which were stable at high temperature.

The probe comprises a solid electrolyte having a mixed subelectrode provided on its surface, and a reference electrode for providing a predetermined oxygen potential is disclosed. The mixed sub-electrode coating on the solid electrolyte includes a mixture of a carbide MC and of an oxide MO of the element M other than carbon of which the carbide is constituted.

5 Claims, 3 Drawing Sheets

PROBE USING A MIXED SUB-ELECTRODE FOR MEASURING THE ACTIVITY OF CARBON IN MOLTON IRON

This application is a continuation of application Ser. No. 07/765,544 filed Sep. 25, 1991, now abandoned.

FIELD OF THE INVENTION

This invention relates to a probe for measuring the activity of carbon as a solute element contained in molten iron.

BACKGROUND OF THE INVENTION

With respect to metallic products, there have recently been many sorts, and the high grades of qualities thereof have progressed, and accordingly observations of the solute elements are important. Almost all cases depend upon extracting samples to be analyzed and, measuring their concentrations by means of instrumental analyses such as an emission spectroscope, but a problem involved therewith was lack of speediness.

In view of such circumstances, there have been made such proposals as methods of rapidly measuring the concentrations or activities of the solute elements contained in the molten metals, at first of Japanese Patent Laid-Open 61-142,455 (Patent Laid-Open 61-260, 155, same 63-191,056, 63-286,760, 63-273,055, 63-309,849, 1-263, 556, 2-73,148, 2-82,153, Utility Model Laid-Open 63-109,643, and same 63-148,867). Basically, these conventional methods immerse, into the molten metal, a probe constituted by forming a coated layer made of an oxide (YOa) of a solute element (Y) or a composite oxide containing said oxide (YOa) on the outer surface of a solid electrolyte having an oxygen ion conductivity, and measure an oxygen partial pressure due to equilibrium reactions between the solute element (Y) and the oxide (YOa) by the principle of an oxygen concentration cell so as to obtain the activities of the solute element (Y).

However, problems thereabout arise that when the oxide (YOa) changes into a gas at a room temperature (e.g., CO, $CO_2$, $NO_2$, $SO_2$, etc.), it cannot be coated on the outer surface of the solid electrolyte, or when the oxide (YOa) changes into the gas (e.g., $P_2O_5$) at the measuring temperature, the coated layer fades away. On the other hand, it may be assumed as one of solving measures that the composite oxide (e.g., $Ca_3(PO_4)_2$, $CaCO_3$, $CaSO_4$, etc.) is employed. However, even in the methods utilizing the composite oxides, there exist no suitable substances stable at high temperature, for example, suitable nitrates for a case of a nitrogen sensor, carbonates for a carbon sensor, or sulfates for a sulfur sensor. For using the sensor in steel making, such oxides or composite oxides are required which remain stable and solid at the temperature of at least 1600° C.

SUMMARY OF THE INVENTION

The present invention has been devised in view of the above mentioned problems, and is to offer a probe for measuring the activity of carbon which could not be measured by the prior art because there existed neither solid oxide nor solid composite oxides which were stable at high temperature.

The probe according to the present invention for measuring the activities of the carbon in the molten iron is basically characterized by coating a sub-electrode (called as "mixed subelectrode" hereinafter) which is composed of a mixture of carbide ($MC_x$) and an oxide ($MO_z$) of element (M) other than the carbon as a measuring object capable of constituting said carbide, on an outer surface of a solid electrolyte employed in conventional oxygen sensors.

In the figures,

1 ... Mixed sub-electrode,
2 ... Solid electrolyte,
3 ... Refererence electrode,
4 ... Lead wire from reference electrode,
5 ... Measuring element,
6 ... Lead wire of working electrode,
7 ... Potentiometer
8 ... Thermocouple,
9 ... Quartz tube,
10 ... Housing,
11 ... Connector,
12 ... Protective tube, and
13 ... Cap

MOST PREFERRED EMBODIMENT FOR PRACTICING THE INVENTION

Explanations will be made to the measuring principle by means of the present probe.

Assume that oxygen is O, the carbon to be a measuring object is C, an element is M which constitutes the carbon and carbides, carbides of said C and M are MCx, and an oxide of M is MOz.

Herein, suffixs "x" and "z" are stoichometric ratio of C to M, and O to M.

When the probe which has the mixed sub-electrode containing MCx and MOz is immersed into the molten iron to be measured, under stated local equilibriums will be realized in a co-existing range of the mixed sub-electrode and the molten iron.

$$\underline{M} + x\underline{C} = MCx \tag{1}$$

$$\underline{M} + Z/2\ O_2 = MOz \tag{2}$$

If M is eliminated from the formulas (1) and (2),

$$x\underline{C} + MOz = MCx + Z/2\ O_2 \tag{3}$$

Assuming that the equilibrium constant of the formula (3) is K, $$K = \frac{aMCx \cdot Po_2^{Z/2}}{aMOz \cdot aC^x} \qquad (4)$$

Since K is the equilibrium constant, K is a function of the temperature only. If keeping constant the activity aMCx of MCx and the activity aMOz of MOz, an activity aC of C may be recognized by measuring a partial pressure Po$_2$ of O and the temperature of the molten iron.

Thus, it is possible to measure the carbon by using the mixed sub-electrode of this invention, which could not be measured in the prior art, since a solid sub-electrode (coating) could not be obtained in the range of an iron melting temperature.

Combinations such as SiC-SiO$_2$, Al$_4$C$_3$-Al$_2$O$_3$ or Cr$_4$C-Cr$_2$O$_3$ may be supposed as the substances for composing the mixed subelectrode. Of course, such substances are not limited to these combinations, but are sufficient, if two substances forming the mixed sub-electrode remain solid at the using temperature and they are coupled such that the ratios of their activities are constant. A third additive may be utilized.

Figure 1:
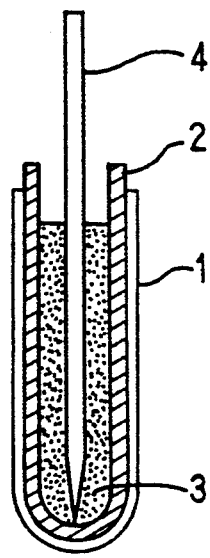
FIG. 1 is a cross sectional view showing one of examples which constitute the measuring element of a probe of the present invention.
Figure 2:
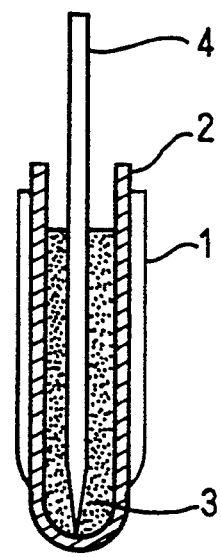
FIG. 2 is a cross sectional view showing another example constituting the measuring elements.
Figure 3:
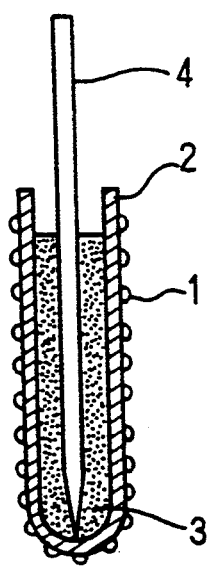
FIG. 3 is a cross sectional view showing a further example constituting the measuring elements thereof.
Figure 4:
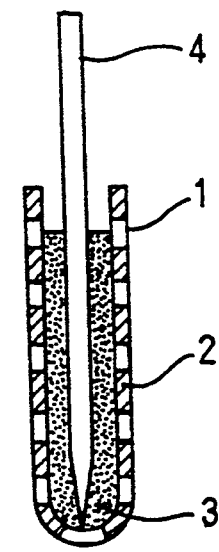
FIG. 4 is a cross sectional view showing a still further example constituting the measuring elements of the same.

The mixed sub-electrode 1 may be formed by any one of the methods for coating it as shown in FIG. 1 on the whole surface of the solid electrolyte 2 which may constitute the oxygen sensor; coating it partially as seen in FIG. 2; in dotting as in FIG. 3; and alternately with the solid electrolyte 2 as in FIG. 4. In these figures, the numeral 3 designates a reference electrode, and the numeral 4 designates a lead wire from a reference electrode. By these illustrated constitutions, the co-existing range of the mixed sub-electrode 1 and the molten iron is formed in the molten iron to be measured, and the local equilibrium is formed.

An explanation will be made to one example of the probes having the inventive composition, referring to FIGS. 5 and 6.

Figure 5:
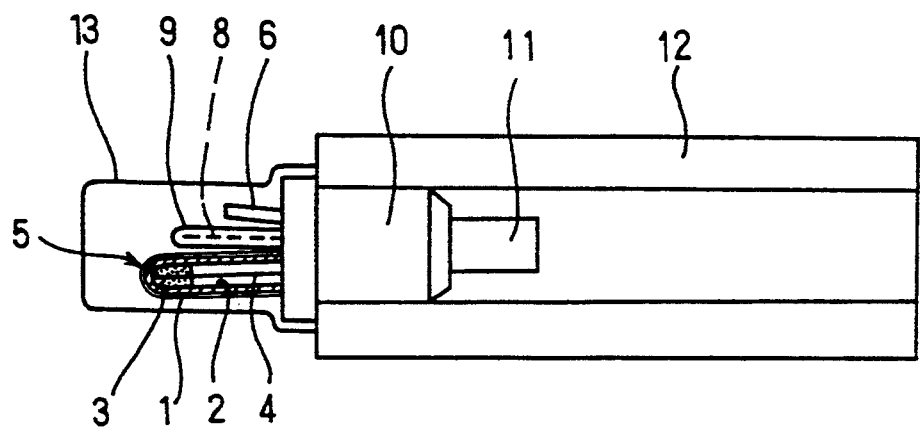
FIG. 5 is an explanatory view of a measuring method by means of a probe having an inventive constituent.

In FIG. 5, the numeral 6 designates a working electrode, the numeral 5 is a measuring element, and the numeral 7 designates a potentiometer. The measuring element 5 is composed of the solid electrolyte 2, a reference electrode 3, the lead wire from a reference electrode 4, and the mixed sub-electrode 1 formed as the coated layer. Basically, the composition is the same as those added with the mixed sub-electrode 1 as the coated layer in the conventional oxygen sensor. The solid electrolyte 2 is sufficient with any ones which have the oxygen ion conductivity at the high temperature and may be used to the conventional oxygen sensor. In the illustrated examples, the solid electrolyte 2 is shaped in tube, into which the reference electrode 3 is inserted.

In the prior art, the solid electrolyte 2 is formed on the outer surface with the coated layer composed of the oxide (YOa) of the solute element (Y) to be measured or the composite oxide including said oxide (YOa), and is immersed into the molten metal for measuring, by the principle of the oxygen concentration cell, the oxygen partial pressure due to the equilibrium reaction between the solute element (Y) and the oxide (YOa), so as to obtain the activity of the solute element (Y).

On the other hand, in the present invention, the coated layer is formed with the mixed sub-electrode 1 which is composed of the mixture of the carbide (MC$_x$) and the oxide (MO$_z$) of the other element (M) than the carbon constituting said carbide (MC$_x$), and is immersed into the molten iron for measuring, by the principle of the oxygen concentration cell, the oxygen partial pressure due to the equilibrium reaction between the carbon existing in the molten iron and the mixed subelectrode 1, so as to obtain the activity of the carbon. Then, an electromotive force EMF is shown with a following formula.

$$EMF = \frac{RT}{F} \ln \frac{Po_2(II)^{\frac{1}{4}} + Pe'^{\frac{1}{4}}}{Po_2(I)^{\frac{1}{4}} + Pe'^{\frac{1}{4}}} \qquad (5)$$

wherein,
F: Faraday's constant
R: Gas constant
T: Absolute temperature of the molten iron
Po$_2$(I): Oxygen partial pressure of the reference electrode
Po$_2$(II): Oxygen partial pressure within the local equilibrium zone
Pet: Parameter of partial electronic conductivity In the formula (5), since Po$_2$(I) and Pe' are functions of the temperature, Po$_2$(II) may be recognized by measuring EMF and T. If Po$_2$(II) is substituted into the formula (4), the activity of the carbon to be the measuring objective may be known.

Figure 6:
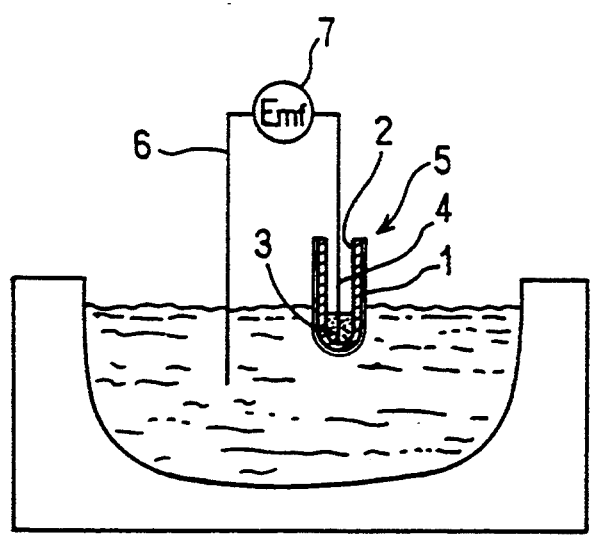
FIG. 6 is an explanatory view showing an outline of the whole probe.

In FIG. 6, this working electrode 6 and the measuring element 5 are secured within a housing 10 together with a quartz tube 9 having a thermocouple 8 therein, and are connected to the potentiometer 7 via a connector 11. Further, the housing 10 is covered with a protective tube 12 and the actual probe is completed by covering the side of the measuring element 5 with a cap 13.

EXAMPLE

The carbon sensor having the inventive structure was used for measuring the activity of the carbon in the molten steel. The specification of the used probe and the conditions of the molten steel are as follows.

A material of the mixed sub-electrode
a mixture of the carbide as SiC and the oxide (MOz)
as
SiO$_2$ of the element other than the carbon constituting
said carbide
A material of the solid electrolyte
ZrO$_2$+MgO (8 mol. %)
A material of the reference electrode
Cr+Cr$_2$O$_3$ (2 wt. %)
A method of coating the mixed sub-electrode
A water and a water glass were added to the
mixture of 1:1 (mol) of SiC and SiO$_2$ to form a
slurry, and said solid electrolyte was dipped into
this slurry and air-dried to form a coated layer.
A measuring temperature
1600° C.
A range of the molten steel composition
%C=0.01 to 1.0
%Si=not more than 0.1
%Mn=not more than 0.1

Figure 7:
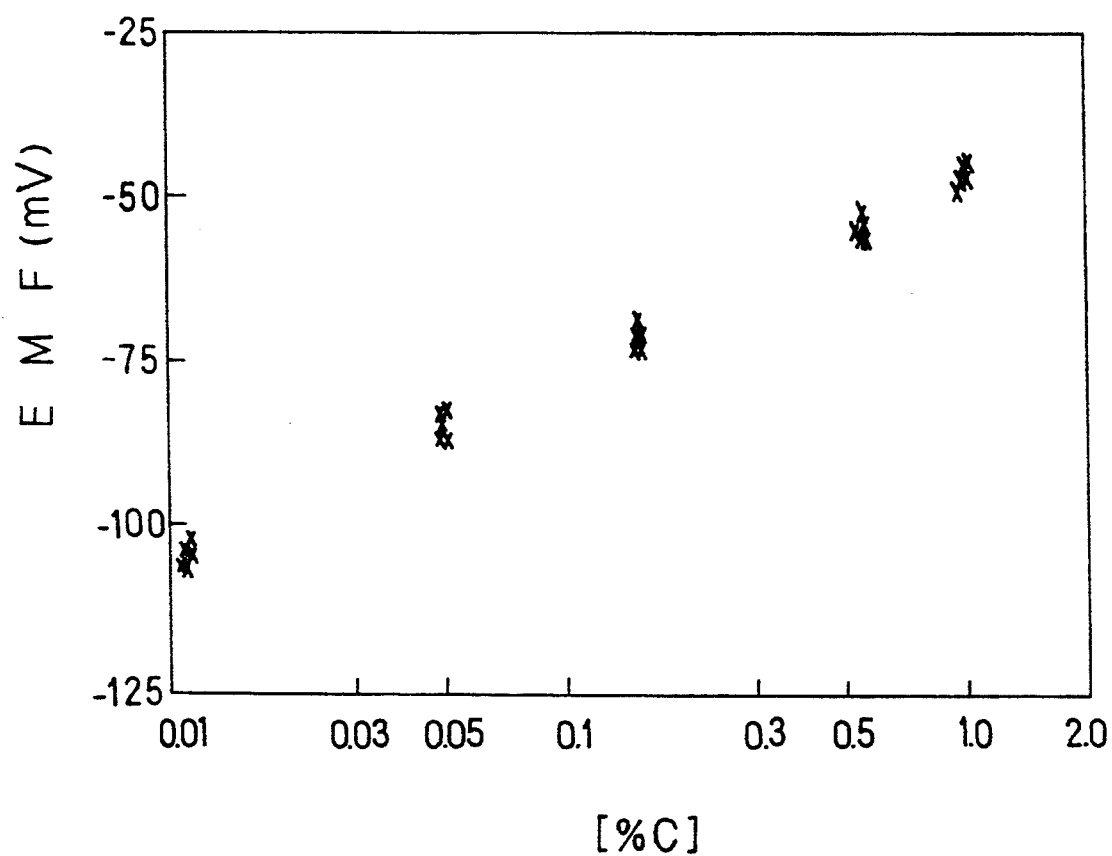
FIG. 7 is a graph showing correlated conditions between measuring results of a carbon sensor pertaining to the examples of this invention and analyzing results from sampling.

FIG. 7 shows the relation between EMF (the electromotive force) measured with said carbon sensor and the carbon concentration (%C) obtained by analyzing the sample.

As shown in the same, a preferable relation could be obtained between EMF (electro motive force) to be measured with the present sensor and the carbon concentration (%C) obtained by analyzing the sample.

A method of calculating the carbon concentration in the molten steel from EMF and the temperature to be measured by the present carbon sensor, is as follows.

If the carbon sensor is immersed into the molten steel, an under mentioned equilibrium relation is realized, corresponding to the above formula (3) with respect to the mixed sub-electrode (SiC and SiO$_2$) and the molten steel surface.

$$C + SiO_2 = SiC + P_2 \tag{6}$$

The equilibrium constant K of this formula (6) is given by a following formular (7).

$$K_{(7)} = \frac{aSiC \cdot Po_2(II)}{aSiO_2 \cdot aC} \tag{7}$$

Further, $K_{(7)}$ of this formula (7) is given as the function of the temperature to a formula (8), and since SiC and SiO$_2$ are pure solids, respective activities aSiC and aSiO$_2$ may be regarded as 1, and the carbon activity aC may be calculated by measuring Po$_2$(II).

$$-RT \, nK_{(7)} = 801400 - 192.56T \; (J/mol) \tag{8}$$

If the carbon activity aC is calculated and divided with the activity coefficient fc of the carbon of a formula (9), the carbon concentration may be obtained.

$$\log fc = 0.243 \times (\text{Carbon concentration}) \tag{9}$$

The above Po$_2$(II) may be obtained by a formula (10) from EMF and the temperature measured by the present sensor.

$$EMF = \frac{RT}{F} \ln \frac{Po_2(II)^{\frac{1}{4}} + Pe'^{\frac{1}{4}}}{Po_2(I)^{\frac{1}{4}} + Pe'^{\frac{1}{4}}} \tag{10}$$

wherein
EMF: Electro motive force to be measured by the present sensor (V)
T: Temperature to be measured by the present sensor (K)
F: Faraday's constant
  2.30521×10$^4$(Cal·V$^{-1}$·mol$^{-1}$)
R: Gas constant
  1.98648 (Cal·deg$^{-1}$·mol$^{-1}$)
Po$_2$(I): The oxygen partial pressure specified with the reference electrode Cr+Cr$_2$O$_3$ Po2(I)=exp (18.636−86384/T)
Pe': Parameter of the partial electronic conductivity Pe' = 10$^{(24.42 - 74370/T)}$
Po$_2$(II): Oxygen partial pressure within the local equilibrium zone

What is claimed is:

1. A probe for measuring the activity of carbon in molten iron, comprising a carbon measuring element and a working electrode, said carbon measuring element comprising a solid electrolyte having oxygen ion conductivity, a reference electrode on an inner surface of said solid electrolyte adapted to assist in measuring partial pressure of oxygen, and a coating on an outer surface of said solid electrolyte and adapted to contact said molten iron, said coating consisting essentially of a mixture of a carbide MC$_x$ and of an oxide MO$_z$ of the element M other than carbon of which said carbide is constituted, wherein x and z are the stoichiometric ratio of C to M and O to M, respectively, said solid electrolyte containing no carbide.

2. A probe according to claim 1, wherein said coating is on the whole outer surface of said solid electrolyte.

3. A probe according to claim 1, wherein said coating is on a part of said outer surface of said solid electrolyte.

4. A probe according to claim 1, wherein said coating is dotted on said outer surface of said solid electrolyte.

5. A probe for measuring the activity of carbon in molten iron, comprising a carbon measuring element and a working electrode, said carbon measuring element comprising a reference electrode adapted to assist in measuring partial pressure of oxygen, a solid electrode having oxygen ion conductivity and a mixed sub-electrode adapted to contact said molten iron and consisting essentially of a mixture of a carbide MC$_x$ and of an oxide MO$_z$ of the element M other than carbon of which said carbide is constituted, wherein x and z are the stoichiometric ratio of C to M and O to M, respectively, said solid electrolyte and said mixed sub-electrode being formed on an outer surface of said reference electrode and alternating with each other in a direction along said outer surface of said reference electrode, said solid electrolyte containing no carbide.

* * * * *